United States Patent
Plessers et al.

(10) Patent No.: US 7,458,286 B2
(45) Date of Patent: Dec. 2, 2008

(54) CARRIER TUBE FOR SENSORS OR SAMPLERS

(75) Inventors: Jacques Plessers, Houthalen-Helchteren (BE); William Biesmans, Zutendaal (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 141 days.

(21) Appl. No.: 11/425,791

(22) Filed: Jun. 22, 2006

(65) Prior Publication Data

US 2007/0000551 A1    Jan. 4, 2007

(30) Foreign Application Priority Data

Jun. 22, 2005    (DE) .................. 10 2005 029 220

(51) Int. Cl.
*G01N 1/12* (2006.01)

(52) U.S. Cl. .............. 73/864.59; 73/864.53; 73/864.51; 73/863.71; 73/864.52

(58) Field of Classification Search ............. 73/864.59, 73/864.53, 864.58, 864.52, 864.51
See application file for complete search history.

(56) References Cited

U.S. PATENT DOCUMENTS

| | | | | | |
|---|---|---|---|---|---|
| 4,037,478 | A | * | 7/1977 | Cure et al. ............... | 73/864.56 |
| 4,250,754 | A | * | 2/1981 | Collins .................... | 73/864.56 |
| 4,317,380 | A | * | 3/1982 | Collins .................... | 73/864.56 |
| 4,875,380 | A | * | 10/1989 | Boron ..................... | 73/864.58 |
| 5,033,320 | A | * | 7/1991 | Baerts ..................... | 73/864.59 |
| 5,421,215 | A | * | 6/1995 | Cure et al. ............... | 73/864.53 |
| 5,752,772 | A | * | 5/1998 | Verstreken et al. ......... | 374/139 |

FOREIGN PATENT DOCUMENTS

| | | |
|---|---|---|
| DE | 2 311 839 | 2/1974 |
| DE | 75 07 605 | 3/1975 |
| DE | 25 37 082 A1 | 3/1976 |
| DE | 103 59 449 B3 | 3/2005 |
| EP | 0 095 102 | 11/1983 |

\* cited by examiner

*Primary Examiner*—Hezron E. Williams
*Assistant Examiner*—Gunnar J Gissel
(74) *Attorney, Agent, or Firm*—Panitch Schwarze Belisario & Nadel LLP

(57) ABSTRACT

A carrier tube is provided for sensors or samplers for use in metal or cryolite melts. The carrier tube has on its exterior surface longitudinal grooves and/or planar surfaces extending in the longitudinal direction of the tube.

12 Claims, 2 Drawing Sheets

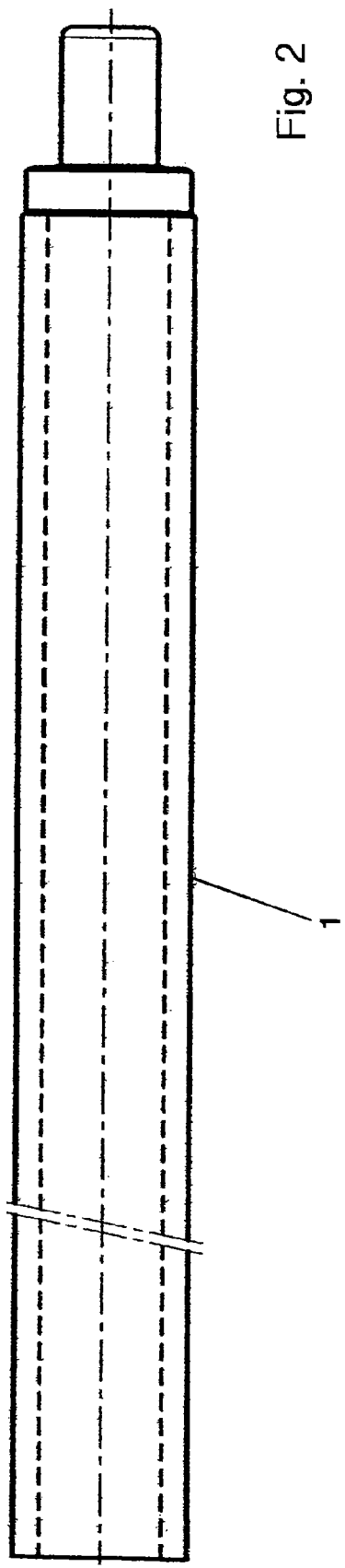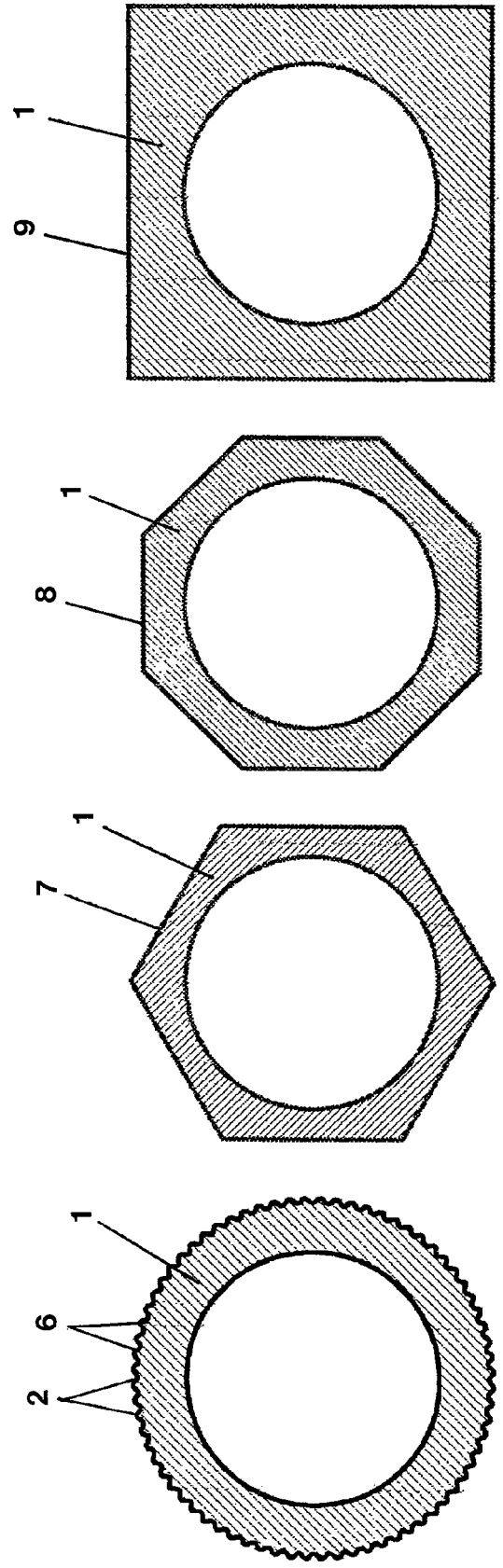

CARRIER TUBE FOR SENSORS OR SAMPLERS

BACKGROUND OF THE INVENTION

The invention relates to a carrier tube for sensors or samplers for use in metal or cryolite melts.

An isolating tube for measuring lances is known from the German utility model G 75 07 605, which is formed from a pressed mixture of cellulose and a binder. Additional carrier tubes are known from German Patent DE 103 59 449 B3.

Sensors with such carrier tubes are packed together in larger numbers. In this connection, the problem frequently arises that the carrier tubes cannot be stored or packed in a stable manner. Carrier tubes with a smooth surface also tend to slide during handling, due to low friction.

BRIEF SUMMARY OF THE INVENTION

The invention is based on the problem of providing an improved carrier tube for sensors or samplers, in particular for use in metal or cryolite melts. The problem is solved in that the carrier tube has on its exterior surface a plurality of longitudinal grooves and/or planar surfaces extending in the longitudinal direction of the carrier tube. In this manner, adjacently arranged carrier tubes contact one another not only along a line on their usually cylindrical surfaces, but they contact one another over a large surface. The friction is thereby increased. Furthermore, a rotational motion is impossible with engagement of longitudinal grooves and/or longitudinal swells arranged between the longitudinal grooves and/or with planar surfaces lying against each other, so that stable storage, packing, and handling is ensured.

Preferably, the longitudinal grooves and/or planar surfaces are arranged evenly distributed over the circumference of the carrier tube. It is particularly beneficial for the material of the carrier tube arranged respectively between two longitudinal grooves (i.e., longitudinal swells) to be provided with an identical cross-section, directed radially outward, as the longitudinal grooves, directed radially inward. In this manner, an exact form-fitting shape of the surface structure of two adjacently arranged carrier tubes is possible.

It is likewise advantageous that the planar surfaces not to be interrupted in their longitudinal progression along the carrier tube by any constructive structures projecting beyond the surface, in order to allow a full-surface contact. Furthermore, it is advantageous for the carrier tube to have longitudinal grooves on its interior side, for example, in order to securely fasten a measuring head or a sample chamber therein.

Additionally, a plug can be arranged preferably at least at one end of the carrier tube, wherein the plug can have longitudinal grooves at the part of its exterior arranged in the carrier tube. Preferably, the plug is connected to the carrier tube in a force-fitting manner. In particular, at least one sensor or one sample chamber can be arranged at or in the plug.

Furthermore, it is advantageous for the carrier tube to be formed from a mixture of a fibrous plant material with starch and/or protein, in particular for it to be formed from a wood or cellulose base.

The carrier tube can be produced in a simple and cost-effective manner by extrusion.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2 is a longitudinal side view, partially shortened and in section, according to another embodiment of a carrier tube of the invention, with a plug in one end; and FIGS. 3a-3d are cross-sectional end views of various embodiments of carrier tubes according the invention.

DETAILED DESCRIPTION OF THE INVENTION

Figure 1:
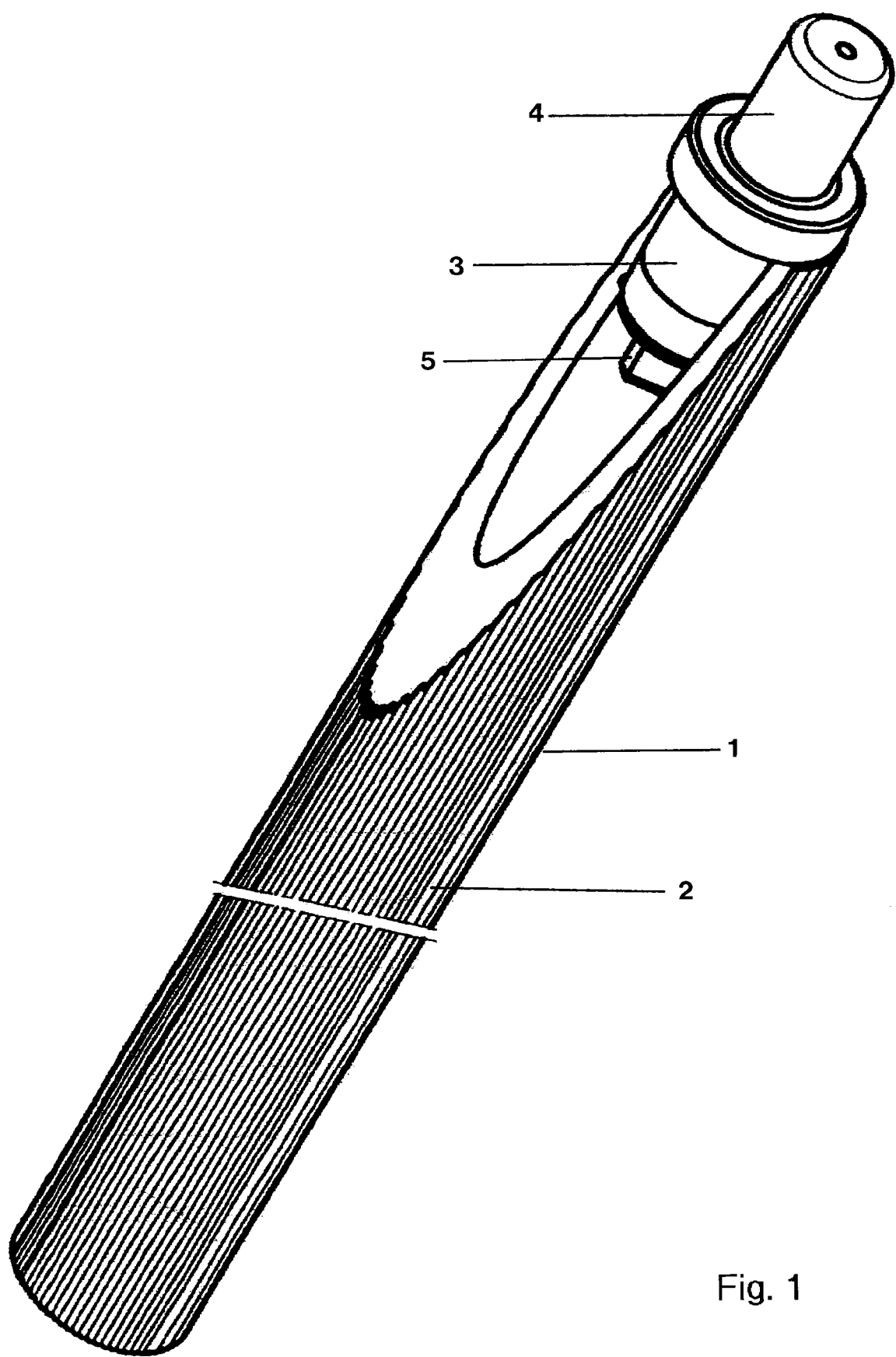
FIG. 1 is a perspective end view, partially in section and partially shortened, of a carrier tube according to one embodiment of the invention, with a plug in the one end.

The carrier tube 1 illustrated in FIG. 1 (partial cross-sectional representation) is provided with a plurality of longitudinal grooves 2 distributed evenly over its circumference. At its one end the carrier tube carries a measuring head 3, which is held in the interior of the carrier tube 1 in a force-fitting manner. The measuring head 3 has several sensors under a protective cap 4, the sensors being connectable via a connector piece 5 to measuring wires guided through the carrier tube 1, in order to forward the measurement signals.

FIG. 2 shows a longitudinal cross-section through a carrier tube 1, while FIGS. 3a-3d show some exemplary cross-sections for the carrier tube 1. FIG. 3a shows a cross-section through a carrier tube according to FIG. 1, which has longitudinal grooves 2 evenly distributed over its circumference. Between the longitudinal grooves 2, swells 6 are naturally arranged. The swells 6 have the same cross-section, directed radially outward, as the longitudinal grooves 2, directed radially inward. With this arrangement, two adjacently lying carrier tubes 1 engage one another in a form-fitting manner, so that rotation against one another is no longer possible.

The cross-sectional views of the carrier tubes 1 illustrated in FIGS. 3b-3d show planar surfaces 7; 8; 9. Optimally, carrier tubes 1 with an identical number of planar exterior surfaces 7; 8; 9 are packed together. The packaging arrangement possible thereby ensures that the tubes cannot rotate against one another, and can be stacked and packed in a stable manner. Additionally, rotation during handling, for example in the hand of an operator, is not possible.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A carrier tube for sensors or samplers, wherein the carrier tube has longitudinal grooves on its exterior surface, and wherein material of the carrier tube arranged respectively between two longitudinal grooves has a same cross-section, directed radially outward, as the longitudinal grooves, directed radially inward.

2. The carrier tube according to claim 1, wherein the longitudinal grooves are arranged evenly distributed over a circumference of the carrier tube.

3. The carrier tube according to claim 1, wherein the carrier tube has longitudinal grooves on its interior surface.

4. The carrier tube according to claim 1, wherein the carrier tube has a plug at least at one end thereof, the plug having longitudinal grooves on its exterior surface arranged in the carrier tube.

5. The carrier tube according to claim 4, wherein the plug is connected to the carrier tube in a force-fitting manner.

6. The carrier tube according to claim 4, wherein at least one sensor or one sample chamber is arranged on or in the plug.

7. The carrier tube according to claim 1, wherein the carrier tube comprises a mixture of a fibrous plant material with at least one of starch and protein.

8. The carrier tube according to claim 7, wherein the carrier tube comprises a wood or cellulose base.

9. The carrier tube according to claim 1, wherein the carrier tube is constructed for use in metal or cryolite melts.

10. A method for producing a carrier tube according to claim 1, wherein the carrier tube is extruded.

11. The carrier tube according to claim 1, wherein two adjacently lying carrier tubes engage one another in a form-fitting manner to prevent rotation of either tube.

12. The carrier tube according to claim 1, wherein multiple carrier tubes can be stacked one above the other.

* * * * *